(12) United States Patent
Ryu et al.

(10) Patent No.: US 11,358,992 B2
(45) Date of Patent: Jun. 14, 2022

(54) CELL-PENETRATING CEREBLON RECOMBINANT FUSION PROTEIN AND USE THEREOF

(71) Applicant: UPPTHERA, Incheon (KR)

(72) Inventors: SooHee Ryu, Incheon (KR); Hwa Jin Lee, Incheon (KR); Seong Hoon Kim, Incheon (KR); Hyeong Seok Lee, Incheon (KR)

(73) Assignee: UPPTHERA, Incheon (KR)

( * ) Notice: Subject to any disclaimer, the term of this patent is extended or adjusted under 35 U.S.C. 154(b) by 0 days.

(21) Appl. No.: 17/244,975

(22) Filed: Apr. 30, 2021

(65) Prior Publication Data

US 2021/0324022 A1 Oct. 21, 2021

Related U.S. Application Data

(63) Continuation of application No. PCT/KR2020/006462, filed on May 15, 2020.

(30) Foreign Application Priority Data

Apr. 17, 2020 (KR) .................. 10-2020-0046840

(51) Int. Cl.
*C07K 19/00* (2006.01)
*C07K 14/47* (2006.01)
*A61K 38/17* (2006.01)
*A61K 45/06* (2006.01)

(52) U.S. Cl.
CPC .......... *C07K 14/4702* (2013.01); *C07K 19/00* (2013.01); *A61K 38/1709* (2013.01); *A61K 45/06* (2013.01); *C07K 2319/10* (2013.01)

(58) Field of Classification Search
CPC .............. C07K 19/00; C07K 14/4702; C07K 2319/10; A61K 38/1709
See application file for complete search history.

(56) References Cited

U.S. PATENT DOCUMENTS

2015/0291562 A1* 10/2015 Crew .................. A61P 9/00
424/94.3

FOREIGN PATENT DOCUMENTS

| KR | 10-2011-0003889 A | 1/2011 | |
|---|---|---|---|
| KR | 10-1626343 B1 | 6/2016 | |
| WO | WO-2014004990 A2 * | 1/2014 | ....... G01N 33/57426 |

OTHER PUBLICATIONS

Zhu, Yuan Xiao, K. Martin Kortuem, and A. Keith Stewart. Leukemia & lymphoma 54.4 (2013): 683-687.
Zhu, Yuan Xiao, et al. Blood cancer journal 9.2 (2019): 1-12.
Franssen, Laurens E., et al. haematologica 103.8 (2018): e368.
Ottis, Philipp, et al. ACS chemical biology 14.10 (2019): 2215-2223.
Gandhi, Anita K., et al. British journal of haematology 164.2 (2014): 233-244.
Chen, Yi-An, et al. Scientific reports 5 (2015): 10667.
Guidotti, Giulia, Liliana Brambilla, and Daniela Rossi. Trends in pharmacological sciences 38.4 (2017): 406-424.
Steinebach, Christian, et al. MedChemComm 10.6 (2019): 1037-1041.
Ryu, Jina, et al. Biotechnology journal 11.11 (2016): 1443-1451.

* cited by examiner

*Primary Examiner* — Zachary C Howard
(74) *Attorney, Agent, or Firm* — Nicholas Park

(57) ABSTRACT

The present invention relates to a novel cell-penetrating recombinant fusion protein including a peptide domain consisting of the amino acid sequence of SEQ ID NO: 1 and a peptide domain consisting of the amino acid sequence of SEQ ID NO: 2. The novel cell-penetrating cereblon recombinant fusion protein according to the present invention may be usefully employed in the prevention or treatment of cereblon-related diseases.

2 Claims, 2 Drawing Sheets

Specification includes a Sequence Listing.

SEQUENCE LISTING

```
<160> NUMBER OF SEQ ID NOS: 4

<210> SEQ ID NO 1
<211> LENGTH: 88
<212> TYPE: PRT
<213> ORGANISM: Artificial Sequence
<220> FEATURE:
<223> OTHER INFORMATION: 30Kc alpha

<400> SEQUENCE: 1

Ala Asp Ser Asp Val Pro Asn Asp Ile Leu Glu Glu Gln Leu Tyr Asn
1               5                   10                  15

Ser Val Val Ala Asp Tyr Asp Ser Ala Val Glu Lys Ser Lys His
            20                  25                  30

Leu Tyr Glu Glu Lys Lys Ser Glu Val Ile Thr Asn Val Val Asn Lys
        35                  40                  45

Leu Ile Arg Asn Asn Lys Met Asn Cys Met Glu Tyr Ala Tyr Gln Leu
    50                  55                  60

Trp Leu Gln Gly Ser Lys Asp Ile Val Arg Asp Cys Phe Pro Val Glu
65                  70                  75                  80

Phe Arg Leu Ile Phe Ala Glu Asn
                85

<210> SEQ ID NO 2
<211> LENGTH: 442
<212> TYPE: PRT
<213> ORGANISM: Homo sapiens

<400> SEQUENCE: 2

Met Ala Gly Glu Gly Asp Gln Gln Asp Ala Ala His Asn Met Gly Asn
1               5                   10                  15

His Leu Pro Leu Leu Pro Ala Glu Ser Glu Glu Glu Asp Glu Met Glu
            20                  25                  30

Val Glu Asp Gln Asp Ser Lys Glu Ala Lys Lys Pro Asn Ile Ile Asn
        35                  40                  45

Phe Asp Thr Ser Leu Pro Thr Ser His Thr Tyr Leu Gly Ala Asp Met
    50                  55                  60

Glu Glu Phe His Gly Arg Thr Leu His Asp Asp Asp Ser Cys Gln Val
65                  70                  75                  80

Ile Pro Val Leu Pro Gln Val Met Met Ile Leu Ile Pro Gly Gln Thr
                85                  90                  95

Leu Pro Leu Gln Leu Phe His Pro Gln Glu Val Ser Met Val Arg Asn
            100                 105                 110

Leu Ile Gln Lys Asp Arg Thr Phe Ala Val Leu Ala Tyr Ser Asn Val
        115                 120                 125

Gln Glu Arg Glu Ala Gln Phe Gly Thr Thr Ala Glu Ile Tyr Ala Tyr
    130                 135                 140

Arg Glu Glu Gln Asp Phe Gly Ile Glu Ile Val Lys Val Lys Ala Ile
```

```
145                 150                 155                 160
Gly Arg Gln Arg Phe Lys Val Leu Glu Leu Arg Thr Gln Ser Asp Gly
                165                 170                 175

Ile Gln Gln Ala Lys Val Gln Ile Leu Pro Glu Cys Val Leu Pro Ser
            180                 185                 190

Thr Met Ser Ala Val Gln Leu Glu Ser Leu Asn Lys Cys Gln Ile Phe
        195                 200                 205

Pro Ser Lys Pro Val Ser Arg Glu Asp Gln Cys Ser Tyr Lys Trp Trp
    210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
            260                 265                 270

Leu Pro Ser Asn Pro Ile Asp Phe Ser Tyr Arg Val Ala Ala Cys Leu
        275                 280                 285

Pro Ile Asp Asp Val Leu Arg Ile Gln Leu Leu Lys Ile Gly Ser Ala
    290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
                325                 330                 335

Ile Phe Ser Leu Ser Leu Cys Gly Pro Met Ala Ala Tyr Val Asn Pro
            340                 345                 350

His Gly Tyr Val His Glu Thr Leu Thr Val Tyr Lys Ala Cys Asn Leu
        355                 360                 365

Asn Leu Ile Gly Arg Pro Ser Thr Glu His Ser Trp Phe Pro Gly Tyr
    370                 375                 380

Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
                405                 410                 415

Leu Thr Arg Ser Ala Leu Leu Pro Thr Ile Pro Asp Thr Glu Asp Glu
            420                 425                 430

Ile Ser Pro Asp Lys Val Ile Leu Cys Leu
        435                 440

<210> SEQ ID NO 3
<211> LENGTH: 530
<212> TYPE: PRT
<213> ORGANISM: Artificial Sequence
<220> FEATURE:
<223> OTHER INFORMATION: 30Kc alpha-CRBN

<400> SEQUENCE: 3

Ala Asp Ser Asp Val Pro Asn Asp Ile Leu Glu Glu Gln Leu Tyr Asn
1               5                   10                  15

Ser Val Val Val Ala Asp Tyr Asp Ser Ala Val Glu Lys Ser Lys His
            20                  25                  30

Leu Tyr Glu Glu Lys Lys Ser Glu Val Ile Thr Asn Val Asn Lys
        35                  40                  45

Leu Ile Arg Asn Asn Lys Met Asn Cys Met Glu Tyr Ala Tyr Gln Leu
    50                  55                  60

Trp Leu Gln Gly Ser Lys Asp Ile Val Arg Asp Cys Phe Pro Val Glu
```

```
                65                  70                  75                  80
        Phe Arg Leu Ile Phe Ala Glu Asn Met Ala Gly Glu Gly Asp Gln Gln
                        85                  90                  95

Asp Ala Ala His Asn Met Gly Asn His Leu Pro Leu Leu Pro Ala Glu
                        100                 105                 110

Ser Glu Glu Asp Glu Met Glu Val Glu Asp Gln Asp Ser Lys Glu
                    115                 120                 125

Ala Lys Lys Pro Asn Ile Ile Asn Phe Asp Thr Ser Leu Pro Thr Ser
        130                 135                 140

His Thr Tyr Leu Gly Ala Asp Met Glu Glu Phe His Gly Arg Thr Leu
        145                 150                 155                 160

His Asp Asp Asp Ser Cys Gln Val Ile Pro Val Leu Pro Gln Val Met
                        165                 170                 175

Met Ile Leu Ile Pro Gly Gln Thr Leu Pro Leu Gln Leu Phe His Pro
                        180                 185                 190

Gln Glu Val Ser Met Val Arg Asn Leu Ile Gln Lys Asp Arg Thr Phe
                    195                 200                 205

Ala Val Leu Ala Tyr Ser Asn Val Gln Glu Arg Glu Ala Gln Phe Gly
        210                 215                 220

Thr Thr Ala Glu Ile Tyr Ala Tyr Arg Glu Glu Gln Asp Phe Gly Ile
        225                 230                 235                 240

Glu Ile Val Lys Val Lys Ala Ile Gly Arg Gln Arg Phe Lys Val Leu
                        245                 250                 255

Glu Leu Arg Thr Gln Ser Asp Gly Ile Gln Gln Ala Lys Val Gln Ile
                    260                 265                 270

Leu Pro Glu Cys Val Leu Pro Ser Thr Met Ser Ala Val Gln Leu Glu
                    275                 280                 285

Ser Leu Asn Lys Cys Gln Ile Phe Pro Ser Lys Pro Val Ser Arg Glu
                    290                 295                 300

Asp Gln Cys Ser Tyr Lys Trp Trp Gln Lys Tyr Gln Lys Arg Lys Phe
        305                 310                 315                 320

His Cys Ala Asn Leu Thr Ser Trp Pro Arg Trp Leu Tyr Ser Leu Tyr
                        325                 330                 335

Asp Ala Glu Thr Leu Met Asp Arg Ile Lys Lys Gln Leu Arg Glu Trp
                        340                 345                 350

Asp Glu Asn Leu Lys Asp Asp Ser Leu Pro Ser Asn Pro Ile Asp Phe
                    355                 360                 365

Ser Tyr Arg Val Ala Ala Cys Leu Pro Ile Asp Asp Val Leu Arg Ile
        370                 375                 380

Gln Leu Leu Lys Ile Gly Ser Ala Ile Gln Arg Leu Arg Cys Glu Leu
        385                 390                 395                 400

Asp Ile Met Asn Lys Cys Thr Ser Leu Cys Cys Lys Gln Cys Gln Glu
                        405                 410                 415

Thr Glu Ile Thr Thr Lys Asn Glu Ile Phe Ser Leu Ser Leu Cys Gly
                    420                 425                 430

Pro Met Ala Ala Tyr Val Asn Pro His Gly Tyr Val His Glu Thr Leu
                    435                 440                 445

Thr Val Tyr Lys Ala Cys Asn Leu Asn Leu Ile Gly Arg Pro Ser Thr
                    450                 455                 460

Glu His Ser Trp Phe Pro Gly Tyr Ala Trp Thr Val Ala Gln Cys Lys
        465                 470                 475                 480

Ile Cys Ala Ser His Ile Gly Trp Lys Phe Thr Ala Thr Lys Lys Asp
                        485                 490                 495
```

Met Ser Pro Gln Lys Phe Trp Gly Leu Thr Arg Ser Ala Leu Leu Pro
                500                 505                 510

Thr Ile Pro Asp Thr Glu Asp Glu Ile Ser Pro Asp Lys Val Ile Leu
        515                 520                 525

Cys Leu
    530

<210> SEQ ID NO 4
<211> LENGTH: 1605
<212> TYPE: DNA
<213> ORGANISM: Artificial Sequence
<220> FEATURE:
<223> OTHER INFORMATION: 30Kc alpha-CRBN

<400> SEQUENCE: 4

| | |
|---|---:|
| ggatccgcag attccgacgt ccctaacgac attctggagg agcagcttta caatagcgtc | 60 |
| gtcgtcgccg attacgacag tgcggttgaa aagagcaagc atttatacga ggagaagaag | 120 |
| agcgaagtca tcacaaatgt cgtgaacaaa ctgatacgaa caacaagat gaactgcatg | 180 |
| gagtacgcct atcaactttg gctccagggc tccaaggaca tcgtccggga ttgtttccca | 240 |
| gttgagttca gacttatctt cgccgaaaac atggccggcg aaggagatca gcaggacgct | 300 |
| gcgcacaaca tgggcaacca cctgccgctc ctgcctgcag agagtgagga agaagatgaa | 360 |
| atggaagttg aagaccagga tagtaaagaa gccaaaaaac caaacatcat aaattttgac | 420 |
| accagtctgc cgacatcaca tacataccta ggtgctgata tggaagaatt tcatggcagg | 480 |
| actttgcacg atgacgacag ctgtcaggtg attccagttc ttccacaagt gatgatgatc | 540 |
| ctgattcccg gacagacatt acctcttcag cttttcacc ctcaagaagt cagtatggtg | 600 |
| cggaatttaa ttcagaaaga tagaaccttt gctgttcttg catacagcaa tgtacaggaa | 660 |
| agggaagcac agtttggaac aacagcagag atatatgcct atcgagaaga acaggatttt | 720 |
| ggaattgaga tagtgaaagt gaaagcaatt ggaagacaaa ggttcaaagt ccttgagcta | 780 |
| agaacacagt cagatggaat ccagcaagct aaagtgcaaa ttcttcccga atgtgtgttg | 840 |
| ccttcaacca tgtctgcagt tcaattagaa tccctcaata agtgccagat atttccttca | 900 |
| aaacctgtct caagagaaga ccaatgttca tataaatggt ggcagaaata ccagaagaga | 960 |
| aagtttcatt gtgcaaatct aacttcatgg cctcgctggc tgtattcctt atatgatgct | 1020 |
| gagaccttaa tggacagaat caagaaacag ctacgtgaat gggatgaaaa tctaaaagat | 1080 |
| gattctcttc cttcaaatcc aatagatttt tcttacagag tagctgcttg tcttcctatt | 1140 |
| gatgatgtat tgagaattca gctccttaaa attggcagtg ctatccagcg acttcgctgt | 1200 |
| gaattagaca ttatgaataa atgtacttcc ctttgctgta acaatgtca agaaacagaa | 1260 |
| ataacaacca aaaatgaaat attcagttta tccttatgtg ggccgatggc agcttatgtg | 1320 |
| aatcctcatg gatatgtgca tgagacactt actgtgtata aggcttgcaa cttgaatctg | 1380 |
| ataggccggc cttctacaga acacagctgg tttcctgggt atgcctggac tgttgcccag | 1440 |
| tgtaagatct gtgcaagcca tattggatgg aagtttacgg ccaccaaaaa agacatgtca | 1500 |
| cctcaaaaat ttggggctt aacgcgatct gctctgttgc ccacgatccc agacactgaa | 1560 |
| gatgaaataa gtccagacaa agtaatactt tgcttgtaac tcgag | 1605 |

CELL-PENETRATING CEREBLON RECOMBINANT FUSION PROTEIN AND USE THEREOF

CROSS-REFERENCE TO RELATED APPLICATION

This application is a US Bypass Continuation Application of International Application No. PCT/KR2020/006462, filed on May 15, 2020 and designating the United States, the International Application claiming a priority date of Apr. 17, 2020 based on prior Korean Patent Application No. 10-2020-0046840, filed on Apr. 17, 2020. The disclosure of which is incorporated herein by reference in its entirety.

BACKGROUND

1. Field of the Invention

The present invention relates to a novel cell-penetrating cereblon recombinant fusion protein and use thereof.

2. Discussion of Related Art

Cereblon is a protein that in humans is encoded by the CRBN gene and forms an E3 ubiquitin ligase complex with damaged DNA binding protein 1 (DDB1), Cullin-4A (CUL4A) and regulator of cullins 1 (ROC1). This complex ubiquitinates a number of other proteins. For example, it is known that this ubiquitination of target proteins by cereblon plays an important role in limb outgrowth in embryos by causing an increase in fibroblast growth factor 8 (FGF8) and fibroblast growth factor 10 (FGF10) levels, and regulating limb and auditory vesicle formation in a number of developmental processes.

Immunomodulatory imide drugs (IMiD) are imide-based drugs that include thalidomide and its analogs such as lenalidomide, pomalidomide, and the like, and are known to have therapeutic efficacy of erythema nodosum leprosum, multiple myeloma, myelodysplastic syndrome, and acute myelogenous leukemia. The key target of IMiD is cereblon, and the mechanism of treatment for multiple myeloma of IMiD is associated with altering complex specificity that induces ubiquitination and degradation of the transcription factors Ikaros (IKZF1) and Aiolos (IKZF3), depending on the binding of IMiD and cereblon. It is known that an increase in expression of cereblon is associated with an improvement in the efficacy of IMiD treatment for multiple myeloma (Zhu et al (2013), and the like.). Conversely, functional abnormalities such as decreased expression or mutation of cereblon results in a decrease in treatment responsiveness to IMiD therapy. This correlation is mainly known in multiple myeloma (Zhu et al (2019), Franssen et al (2018), and the like.)

Meanwhile, focusing on an IMiD binding ability to cereblon which is an E3 ubiquitin ligase, the technology of proteolysis targeting chimera (PROTAC) which is a compound that induces disease proteolysis, has recently been in the spotlight. The PROTAC compound is a bifunctional compound in which a ligand molecule that binds to a disease-related target protein and an E3 ubiquitin ligase-binding moiety are linked, and induces proteolysis of the target protein in the body. It has been reported that in the case of the lack of cereblon function, just as IMiD resistance is caused, resistance of cereblon PROTAC using IMiD is also induced (Ottis et al. (2019), and the like.).

Therefore, there is an unsatisfied demand for a novel drug for improving the function of cereblon-targeting drugs by restoring cereblon dysfunction. There have been attempts to treat cereblon-related diseases at the gene level, such as artificially regulating cereblon expression. However, it is known that there is little correlation between the mRNA level and the protein level in cells in which cereblon dysfunction is reported, and thus there are certain limitations (Gandhi et al. (2014), and the like.).

Meanwhile, it has been known that the method for artificially expressing the cereblon protein itself and introducing the protein into target cells is very inadequate as a method for recovering cereblon dysfunction in consideration that the half-life of the cereblon protein itself is known to be very unstable at about 0.6 h (Chen et al. (2015), and the like.). Moreover, a method for introducing an exogenous protein into a cell is very limited in its use because the high molecular weight protein is not capable of penetrating the cell membrane of the target cell.

There is a method for conjugating a cell-penetrating peptide to penetrate the intracellular transport protein. However, when a protein-level conjugate is added to the cereblon, depending on the conjugation site, the formation of the E3 ubiquitin ligase complex may fail in cells due to structural steric hindrance, and there may be a problem in which a drug originally bound is not bound. Therefore, it is very difficult to predict whether the function of cereblon will be fully exhibited by simply conjugating a cell-penetrating peptide to cereblon.

In the case of cell-penetrating peptides, the most studied cell-penetrating peptide is a transactivator of transcription (TAT) protein derived from human immunodeficiency virus-1 (HIV-1). It is known that a peptide consisting of 47th to 57th amino acids in the TAT protein composed of 86 amino acids has a cell-penetrating function. Similarly, it is known that amino acids 267 to 300 of the VP22 protein of HSV-1, amino acids 339 to 355 of the Antennapedia (Antp) of a *drosophila*, artificially synthesized positively charged peptides, and the like, function as cell-penetrating peptides. Based on these facts, studies have been conducted in which cargo substances such as proteins or nucleic acids are bound to cell-penetrating peptides and delivered into cells (Guidotti et al. (2017)).

Meanwhile, 30Kc19 protein is a protein having a size of about 28 kDa derived from the hemolymph of silkworm (*Bombyx mori*), and has been applied to various studies since this protein has anti-apoptotic activity, protein stabilization or solubility enhancement function, and the like. Korean Patent Laid-Open Publication No. 10-2011-0003889 discloses the function of a cell-penetrating peptide of 30Kc19 protein as the cell-penetrating peptide. Korean Patent Registration No. 10-1626343 discloses cell penetrating function of the α-helix domain (30Kc19α) of the 30Kc19 protein.

SUMMARY OF THE INVENTION

An object of the present invention is to provide a recombinant fusion protein including cereblon linked to a cell-penetrating peptide domain.

Another object of the present invention is to provide a nucleic acid encoding the recombinant fusion protein, a recombinant vector containing the nucleic acid, a host cell transformed with the recombinant vector, and a method for preparing a recombinant fusion protein using the host cell.

Still another object of the present invention is to provide a use for preventing or treating a cereblon-related disease according to the use of the recombinant fusion protein alone or in combination with a cereblon targeting drug.

BRIEF DESCRIPTION OF THE DRAWINGS

Example embodiments will be described in more detail with regard to the figures, wherein like reference numerals refer to like parts throughout the various figures unless otherwise specified, and wherein.

DETAILED DESCRIPTION OF EXEMPLARY EMBODIMENTS

Figure 1:
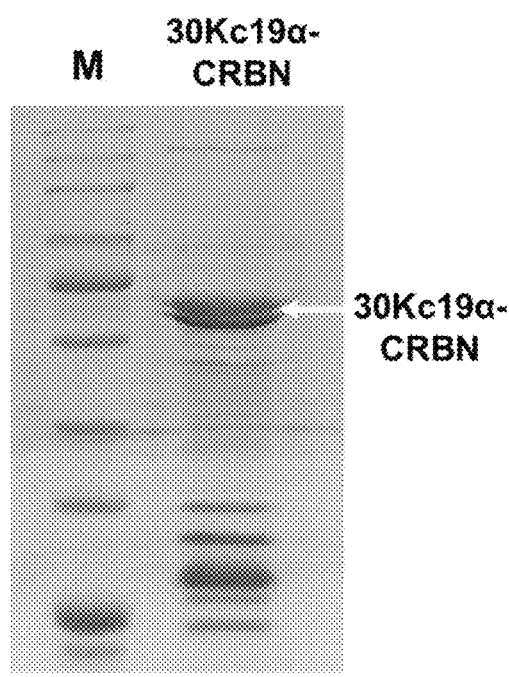
FIG. 1 is an image showing preparation results of the cell-penetrating cereblon recombinant fusion protein according to the present invention.

The present inventors prepared a novel recombinant fusion protein including a cell-penetrating peptide consisting of an α-helix domain (30Kc19α) of 30Kc19 protein and cereblon linked to the cell-penetrating peptide domain, confirmed that therapeutic effects for cereblon-related diseases were remarkably excellent when the recombinant fusion protein was used in combination with a cereblon targeting drug, and completed the present invention.

Accordingly, the present invention provides a recombinant fusion protein including 30Kc19a and cereblon, a preparation method thereof, and a use for preventing or treating a cereblon-related disease using the same, and the like.

Cell-Penetrating Cereblon Recombinant Fusion Protein

In one general aspect, the present invention provides a recombinant fusion protein including a cell-penetrating peptide domain consisting of a 30Kc19 protein α-helix domain (30Kc19α) and a cereblon linked to the cell-penetrating peptide domain.

In the present invention, the 30Kc19 protein α-helix domain (30Kc19α) refers to an α-helix domain having a cell penetrating function in the 30Kc19 protein derived from a silkworm (*Bombyx mori*). Specifically, 30Kc19α is a domain (SEQ ID NO: 1) consisting of amino acid sequences 1 to 88 of Chain A, 30k Protein 1 (PDB: 4IY8_A), which is a member of the 30 KDa lipoprotein family derived from the silkworm (*Bombyx mori*) consisting of a total of 239 amino acids. In an embodiment, 30Kc19α consists of the amino acid sequence of SEQ ID NO:1.

In the present invention, cereblon refers to a protein encoded by the CRBN gene. Cereblon has been reported to be a key molecular target that binds to thalidomide and has a highly conserved sequence from plants to humans (ITo, 2010, et al.). In an embodiment, the cereblon is human cereblon isoform 1 (NCBI Reference Sequence: NP_057386.2; SEQ ID NO: 2) consisting of a total of 424 amino acids. In an embodiment, 30Kc19α consists of the amino acid sequence of SEQ ID NO:2.

In an embodiment, 30Kc19α consists of the amino acid sequence of SEQ ID NO: 1 and the cereblon consists of the amino acid sequence of SEQ ID NO: 2. In an embodiment, the recombinant fusion protein of the present invention consists of the amino acid sequence of SEQ ID NO: 3.

In an aspect, the present invention provides a cell-penetrating recombinant fusion protein including a peptide domain consisting of the amino acid sequence of SEQ ID NO: 1 and a peptide domain consisting of the amino acid sequence of SEQ ID NO: 2.

In an embodiment, the recombinant fusion protein consists of a peptide domain consisting of the amino acid sequence of SEQ ID NO: 1 and a peptide domain consisting of the amino acid sequence of SEQ ID NO: 2.

In an embodiment, in the recombinant fusion protein, a peptide domain consisting of the amino acid sequence of SEQ ID NO: 2 is linked to the carboxyl-terminus of the peptide domain consisting of the amino acid sequence of SEQ ID NO: 1.

In an embodiment, in the recombinant fusion protein, a peptide domain consisting of the amino acid sequence of SEQ ID NO: 1 is linked to the amino-terminus of the peptide domain consisting of the amino acid sequence of SEQ ID NO: 2.

In an embodiment, in the recombinant fusion protein, the carboxyl-terminus of the peptide domain consisting of the amino acid sequence of SEQ ID NO: 1 is linked to the carboxyl-terminus of the peptide domain consisting of the amino acid sequence of SEQ ID NO: 2.

In the present invention, the recombinant fusion protein includes not only the specified amino acid sequence structure, but also a protein variant that performs a biological function equivalent thereto. Herein, the protein variant refers to a protein having one or more amino acid mutations or modifications compared with the reference recombinant fusion protein of the present invention, for example, may be prepared by substitution, deletion, insertion and/or chemical modification in one or more amino acids in the existing amino acid sequence.

In an embodiment, the protein variant includes conservative amino acid substitutions that do not significantly affect the function of the reference recombinant fusion protein of the present invention. The conservative substitutions may include basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan, and tyrosine), and small amino acids (glycine, alanine, serine and threonine). In general, amino acid substitutions that do not alter specific activity are known in the art to which the present invention pertains. The most common exchanges include Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu and Asp/Gly, and other examples of the conservative amino acid substitutions are shown in Table 1 below.

TABLE 1

| Original Amino Acid | Exemplary Residue Substitution | Preferred Residue Substitution |
|---|---|---|
| Ala(A) | Val, Leu, Ile | Val |
| Arg(R) | Lys, Gln, Asn | Lys |
| Asn(N) | Gln, His, Asp, Lys, Arg | Gln |
| Asp(D) | Glu, Asn | Glu |
| Cys(C) | Ser, Ala | Ser |
| Gln(Q) | Asn, Glu | Asn |
| Glu(E) | Asp, Gln | Asp |
| Gly(G) | Ala | Ala |
| His(H) | Asn, Gln, Lys, Arg | Arg |
| Ile(I) | Leu, Val, Met, Ala, Phe | Leu |
| Leu(L) | Ile, Val, Met, Ala, Phe | Ile |
| Lys(K) | Arg, Gln, Asn | Arg |
| Met(M) | Leu, Phe, Ile | Leu |

TABLE 1-continued

| Original Amino Acid | Exemplary Residue Substitution | Preferred Residue Substitution |
| --- | --- | --- |
| Phe(F) | Leu, Val, Ile, Ala, Tyr | Tyr |
| Pro(P) | Ala | Ala |
| Ser(S) | Thr | Thr |
| Thr(T) | Ser | Ser |
| Trp(W) | Tyr, Phe | Tyr |
| Tyr(Y) | Trp, Phe, Thr, Ser | Phe |
| Val(V) | Ile, Leu, Met, Phe, Ala | Leu |

In an embodiment, the cell-penetrating peptide domain in the recombinant fusion protein according to the present invention is a protein variant having an amino acid sequence with at least 80%, 85%, 90%, 95%, 96%, 97%, 98% or 99% homology to the amino acid sequence of SEQ ID NO: 1. In an embodiment, the cell-penetrating peptide domain is a conservative amino acid substitute for the amino acid sequence of SEQ ID NO: 1.

In an embodiment, the cereblon in the recombinant fusion protein according to the present invention is a protein variant having an amino acid sequence with at least 80%, 85%, 90%, 95%, 96%, 97%, 98% or 99% homology to the amino acid sequence of SEQ ID NO: 2. In an embodiment, the cereblon is a conservative amino acid substitute for the amino acid sequence of SEQ ID NO: 2.

In an embodiment, the recombinant fusion protein according to the present invention is a protein variant having an amino acid sequence with at least 80%, 85%, 90%, 95%, 96%, 97%, 98% or 99% homology to the amino acid sequence of SEQ ID NO: 3. In an embodiment, the recombinant fusion protein is a conservative amino acid substitute for the amino acid sequence of SEQ ID NO: 3.

In the present invention, the recombinant fusion protein refers to a protein in a form in which amino acid sequences of different origins are combined into one polypeptide chain by in-frame combination of nucleotide sequences encoding the amino acid sequences, and includes an internal fusion in which a sequence of a different origin is inserted into a polypeptide chain, as well as being fused to one of ends of the polypeptide chain. The fusion protein may be a recombinant protein prepared from any one selected from the group consisting of *E. coli*, yeast, insect cells, and mammalian cells by a gene recombination method. The recombinant fusion protein according to the present invention may be encoded by a nucleic acid molecule.

Nucleic Acid Encoding Cell-Penetrating Cereblon Recombinant Fusion Protein and Recombinant Vector Including the Same In an aspect, the present invention provides a nucleic acid encoding the recombinant fusion protein as described above and/or a recombinant vector including the same.

In the present invention, those of ordinary skill in the art will appreciate that in consideration of codon degeneracy or preferred codon in a organism to which the recombinant fusion protein is intended to be expressed, the nucleic acid encoding the recombinant fusion protein may be variously modified in a coding region within a range in which the amino acid sequence of the recombinant fusion protein expressed from the coding region is not altered, may be subjected to various modifications or alterations even in a region except the coding region, provided that it does not affect the expression of the gene, and such modified genes are also included in the scope of the present invention. In other words, as long as the nucleic acid of the present invention encodes a protein having an activity equivalent thereto, one or more nucleic acid bases may be mutated by substitution, deletion, insertion, or a combination thereof, and these are also included in the scope of the present invention.

In the present invention, the recombinant vector is a vehicle capable of introducing a foreign nucleic acid into a host cell, transforming the host cell, and promoting expression of the introduced nucleic acid, which is used with the same meaning as commonly used in the technical field to which the present invention pertains.

In an embodiment, the recombinant vector is a plasmid vector, a cosmid vector, a viral vector or an artificial chromosomal vector. The plasmid vector is a DNA molecule capable of easily accommodating foreign DNA and being easily introduced into the host cell, which is used with the same meaning as commonly used in the technical field to which the present invention pertains. A typical plasmid vector has a structure including (a) the origin of replication for efficient replication to contain hundreds of plasmid vectors per a host cell, (b) a selectable marker that allows the host cell transformed with a plasmid vector to be selected, and (c) a restriction enzyme cleavage site into which foreign DNA fragments are capable of being inserted. Even if an appropriate restriction enzyme cleavage site does not exist, the vector and foreign DNA are able to be easily ligated when using a synthetic oligonucleotide adapter or linker according to a conventional method. Non-limiting examples of the plasmid vector may include, but are not limited to, pKK plasmid (Clonetech), pUC plasmid, pET plasmid (Novagen, Inc., Madison, Wis.), pRSET or pREP plasmid (Invitrogen, San Diego, Calif.), or pMAL plasmid (New England Biolabs, Beverly, Mass.).

In an embodiment, the viral vector may be a DNA viral vector or an RNA viral vector, and may be a bacteriophage, an animal virus, or a plant virus. For example, the viral vector may be vaccinia virus, adenovirus, adeno-associated virus (AAV), lentivirus, retrovirus, or herpes virus, but is not limited thereto.

In an embodiment, the recombinant vector includes a nucleic acid consisting of the amino acid sequence of SEQ ID NO: 4.

In an embodiment, the recombinant vector includes a promoter operably linked to a nucleic acid encoding a recombinant fusion protein according to the present invention. In the present invention, the term "operably linked" means that a specific nucleic acid is linked to another nucleic acid so as to exert function thereof. In other words, the fact that a gene encoding the specific protein or peptide is operably linked to a promoter means that the corresponding gene is capable of being transcribed into mRNA by the promoter and translated into a protein or peptide.

Host Cell for Preparing Cell-Penetrating Cereblon Recombinant Fusion Protein and Preparation Method Thereof In an aspect, the present invention provides a host cell transformed with the recombinant vector as described above and/or a method for preparing a recombinant fusion protein using the same.

In the present invention, the term "transformation" refers to a process of introducing a gene into a host cell to be capable of being expressed in the host cell, wherein the transformed gene includes any gene without limitation, either inserted into chromosome of the host cell or presented in the outside of chromosome as long as it is capable of being expressed in the host cell. In addition, the gene includes DNA and RNA as nucleic acids capable of encoding a polypeptide. Any type of gene is usable without limitation as long as the gene is capable of being introduced and expressed into the host cell. A method for transforming by introducing the recombinant vector of the present invention into the host cell includes methods known in the technical field to which the present invention pertains, using a recombinant vector containing the DNA of the present invention, such as transient transfection, microinjection, transduction, cell fusion, calcium phosphate precipitation, liposome-mediated transfection, DEAE dextran-mediated transfection, polybrene-mediated transfection, electroporation, and the like, but the method is not limited thereto.

In an embodiment, the host cell may be prokaryotic cells such as *E. coli*; fungi such as yeast; plant cells; or mammalian cells such as an insect cell or a plant cell, and may be a cell line derived from the cell. Non-limiting examples of the cell line may include, but are not limited to, CHO, HeLa, COST, COP5, HEK293, HEK293T, HepG2, CV1, BHK, TM4, VERO-76, MDCK, W138, and the like. A person skilled in the art may appropriately select the type of host cell suitable for preparation of the recombinant protein.

In an aspect, the present invention provides a method for preparing a recombinant fusion protein containing 30Kc19α and cereblon including: culturing the host cell described above; inducing expression of a protein from the cultured host cell; and recovering the expressed protein.

The method for culturing the host cell, the method for inducing expression of the protein, and the method for recovering the expressed protein that are suitable for preparing the recombinant fusion protein are known in the technical field to which the present invention pertains, and a person skilled in the art can appropriately select a method for effectively expressing the recombinant fusion protein according to the present invention using the above-described vector and host cell.

Pharmaceutical Uses and Co-Administration of Cell-Penetrating Cereblon Recombinant Fusion Protein The cell-penetrating cereblon recombinant fusion protein described above may be usefully employed as pharmaceuticals.

In an aspect, the present invention provides a pharmaceutical composition for preventing or treating a cereblon-related disease including the recombinant fusion protein containing a cell-penetrating peptide domain consisting of an α-helix domain (30Kc19α) of 30Kc19 protein and cereblon linked to the cell-penetrating peptide domain.

Figure 2:
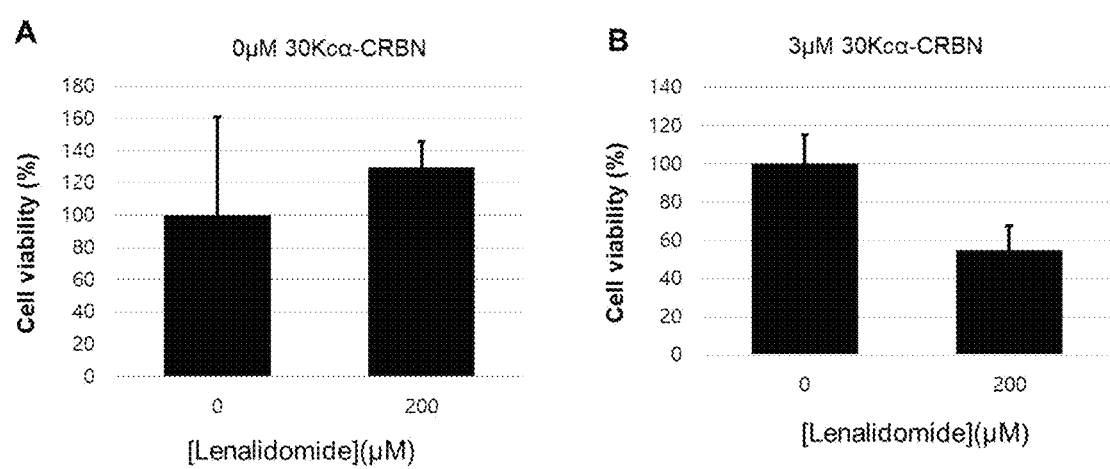
FIG. 2 is a graph showing cell viability after treatment with the cell-penetrating cereblon recombinant fusion protein according to the present invention in lenalidomide-resistant multiple myeloma cells.

It has been considered that expression of the cereblon recombinant protein itself for the treatment of the cereblon-related disease is a very unfavorable method since the half-life of the cereblon protein is very short, so it is unstable. In spite of the negative recognition in the art as described above, the present inventors have succeeded in solving the stability problem of the existing cereblon protein and at the same time introducing normal cereblon activity into cells by introducing a recombinant fusion protein that binds a specific cell-penetrating peptide to cereblon having low stability (FIG. 2).

In the present invention, the cereblon-related disease refers to any disease that is caused by dysfunction of cereblon in the body and/or that is capable of being prevented, ameliorated, improved or treated by enhancing the activity of cereblon. The dysfunction of cereblon may be caused by a decrease in expression of cereblon and/or cereblon mutation, or the like.

In the present invention, the cereblon mutation includes cereblon mutations that have been reported to be associated with genetic diseases. For example, the C391R mutation in which the 391th cysteine of the amino acid sequence of SEQ ID NO: 2 is substituted with arginine has been significantly reported in patients with Autosomal-recessive non-syndromic intellectual disability (ARNS-ID) (Sheereen et al. Journal of Medical Genetics 54.4 (2017): 236-240.]). In the present invention, cereblon-related disease includes cereblon mutation-related genetic diseases.

In the present invention, the cereblon mutation is a mutation resulting from substitution, deletion or insertion of one or more amino acids in cereblon, in addition to the clinically confirmed cereblon mutation, and is included without limitation as long as the mutation causes dysfunction of cereblon.

The cereblon-related disease may be cancer, an autoimmune disease, or an inflammatory disease.

In the present invention, cancer means cellular disorders characterized by unregulated or dysregulated cell proliferation, reduced cellular differentiation, improper ability to invade surrounding tissues, and/or the ability to establish new growth at ectopic sites. As a non-limiting example, the cancer may be one or more selected from the group consisting of pseudomyxoma, intrahepatic biliary tract cancer, hepatoblastoma, liver cancer, thyroid cancer, colon cancer, testicular cancer, myelodysplastic syndrome, glioblastoma, oral cancer, lip cancer, mycosis, acute myelogenous leukemia, acute lymphocytic leukemia, basal cell carcinoma, ovarian epithelial carcinoma, ovarian germ cell carcinoma, male breast cancer, brain cancer, pituitary adenoma, multiple myeloma, gallbladder cancer, biliary tract cancer, colon cancer, chronic myelogenous leukemia, chronic lymphocytic leukemia, retinoblastoma, choroidal melanoma, diffuse large B-cell lymphoma, ampulla of vater cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, pediatric brain cancer, pediatric lymphoma, pediatric leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureter cancer, urethral cancer, primary site unknown cancer, gastric lymphoma, gastric cancer, gastric carcinoma, gastrointestinal epilepsy, Wilms cancer, breast cancer, sarcoma, penile cancer, pharyngeal cancer, pregnancy chorionic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cord cancer, vestibular schwannoma, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, and thymic cancer. Further, preferably, the cancer may be one or more selected from the group consisting of acute myeloid leukemia (AML); chronic myelogenous leukemia (CML); acute lymphoblastic leukemia (ALL); chronic lymphocytic leukemia (CLL); Hodgkin's disease (HD); non-Hodgkin's lymphoma (NHL); B-cell lymphoma; T-cell lymphoma; multiple myeloma (MM); amyloidosis; Waldenstrom's macroglobulinemia; myelodysplastic syndrome (MDS); small lymphocytic lymphoma (SLL); marginal zone lymphoma; asymptomatic multiple myeloma; and myeloproliferative syndrome.

The cancer of the present invention is preferably multiple myeloma. From Examples of the present invention, a cell-penetrating cereblon recombinant fusion protein was prepared, and it was confirmed that when administered in combination with lenalidomide which is an anticancer agent in multiple myeloma, anticancer effects were remarkably improved (FIG. 2).

The autoimmune disease refers to a disease involving an inadequate response of the immune system to an autoantigen. As a non-limiting example, the autoimmune disease may be one or more selected from the group consisting of graft-versus-host disease (GvHD), immune neutropenia, Guillain-Barre syndrome, epilepsy, autoimmune encephalitis, Isaac's syndrome, nevus syndrome, *Pemphigus vulgaris*, *Pemphigus foliaceus*, bullous pemphigoid, acquired bullous epidermolysis, pemphigoid gestationis, mucos membrane-like blister, antiphospholipid syndrome, autoimmune anemia, autoimmune Grave disease, Goodpasture syndrome, myasthenia gravis, multiple sclerosis, rheumatoid arthritis, lupus, idiopathic thrombocytopenia purpura (ITP), lupus nephritis, and membranous nephropathy.

The inflammatory disease refers to a disease accompanying inflammation as a major lesion. The inflammatory disease may be, for example, one or more selected from the group consisting of sepsis, gastritis, enteritis, nephritis, hepatitis, chronic obstructive pulmonary disease (COPD), erythema nodosum leprosum, pulmonary fibrosis, irritable bowel syndrome, inflammatory pain, migraine, headache, back pain, fibromyalgia, fascia disease, viral infection, bacterial infection, fungal infection, burns, wounds from surgical or dental surgery, hyperprostaglandin syndrome, atherosclerosis, gout, Hodgkin's disease, pancreatitis, conjunctivitis, iritis, scleritis, uveitis, and eczema.

In an embodiment, the cereblon-related disease has resistance to cereblon-targeting drugs. In the present invention, the drug resistance refers to a condition in which a disease responds weaker than expected or does not respond to treatment of drug or drugs. The drug resistance may be inherent in that the disease has low or no reactivity to the drug or drugs from the beginning, or may be acquired, meaning that the response to the drug or drugs to which the disease has previously reacted is reduced or stopped.

In the present invention, the cereblon-targeting drug refers to a pharmaceutical substance having cereblon binding activity. Specifically, the cereblon-targeting drug includes, but is not limited to, an immunomodulatory drug (IMiD), a cereblon-targeting bifunctional compound (or PROTAC), or a combination thereof.

In the present invention, the immunomodulatory drug is an immunomodulatory functional compound containing an imide group, and includes thalidomide, lenalidomide, pomalidomide, and the like. The term immunomodulatory drug has a clearly defined meaning in the technical field to which the present invention pertains, and standards for whether any compound is an immunomodulatory drug are known in the art (International Patent Publication Nos. WO2014/004990, WO2015/085172, and the like.). The immunomodulatory drug specifically includes, but is not limited to, lenalidomide, pomalidomide, thalidomide, or a combination thereof. It was confirmed from Examples of the present invention that when the cell-penetrating cereblon recombinant fusion protein was treated with lenalidomide-resistant cancer, the cancer survival rate was significantly reduced (FIG. 2).

In the present invention, the cereblon-targeting bifunctional compound refers to a bifunctional compound consisting of a moiety that binds to cereblon and a moiety that targets any disease protein. This bifunctional compound is referred to as proteolysis targeting chimera (PROTAC) in the art. It is known that the cereblon-targeting bifunctional compound is capable of effectively degrading the disease protein by employing cereblon-binding ability and disease protein-binding ability and making the disease protein close to cereblon protein which is the E3 ubiquitin ligase (International Patent Publication Nos. WO2015/160845, WO2018/144649, and the like).

In an aspect, the present invention provides a combination for preventing or treating a cereblon-related disease including: a first pharmaceutical composition containing the cell-penetrating cereblon recombinant fusion protein as described above; and a second pharmaceutical composition containing a cereblon-targeting drug.

Descriptions of the cereblon-targeting drug and the cereblon-related disease are the same as described above.

In the composition, the first pharmaceutical composition and the second pharmaceutical composition are administered simultaneously or at the different times.

In an aspect, the present invention provides a pharmaceutical composition for a cereblon-targeting drug adjuvant containing the cell-penetrating cereblon recombinant fusion protein as described above.

In the present invention, the term "drug adjuvant" refers to a use in which the medicinal effect is relatively low when administered alone, but the efficacy of the cereblon-targeting drug is remarkably improved when administered in combination with the cereblon-targeting drug.

It was confirmed from Examples of the present invention that the cell-penetrating cereblon recombinant fusion protein significantly enhanced the therapeutic efficacy of an immunomodulatory drug against multiple myeloma cells (FIG. 2). Therefore, the cell-penetrating cereblon recombinant fusion protein of the present invention may be usefully employed as the cereblon-targeting drug adjuvant.

For administration, the composition of the present invention may contain a pharmaceutically acceptable salt of the above-described cell-penetrating cereblon recombinant fusion protein, carrier, excipient, diluent, solubilizer, and the like.

The pharmaceutically acceptable salt refers to a salt commonly used in the pharmaceutical industry, and for example, may include salts of inorganic ions such as sodium, potassium, calcium, magnesium, lithium, copper, manganese, zinc, iron, and the like, salts of inorganic acids such as hydrochloric acid, phosphoric acid, sulfuric acid, and the like, and in addition thereto, may include salts of organic acids such as ascorbic acid, citric acid, tartaric acid, lactic acid, maleic acid, malonic acid, fumaric acid, glycolic acid, succinic acid, propionic acid, acetic acid, orotic acid, acetylsalicylic acid, and the like, and amino acid salts such as lysine, arginine, guanidine, and the like. Further, there are salts of organic ions, such as tetramethyl ammonium, tetraethyl ammonium, tetrapropyl ammonium, tetrabutyl ammonium, benzyl trimethyl ammonium, benzethonium, and the like, that are capable of being used in pharmaceutical reactions, purification and separation processes. However, types of salts meant in the present invention are not limited to salts that are listed above.

Examples of the carrier, excipient and diluent may include, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils. Examples of the solubilizer may include, but are not limited to, poloxamer, labrasol, and the like.

The pharmaceutical composition of the present invention may be prepared in a pharmaceutical formulation using a method well known in the art. In the preparation of the formulation, the active ingredient may be mixed or diluted with the carrier, or encapsulated in a carrier in the form of a container. When the pharmaceutical composition of the present invention is prepared in a dosage form for oral administration, for example, may be formulated as tablets, troches, lozenges, water-soluble or oily suspensions, formulated powders or granules, emulsions, hard or soft capsules, syrups or elixirs.

The pharmaceutical composition may be administered by oral, rectal, transdermal, intravenous, intramuscular, intraperitoneal, intramedullary, intrathecal or subcutaneous route. A formulation for oral administration may be tablets, pills, soft or hard capsules, granules, powders, liquids, or emulsions, but is not limited thereto. A formulation for parenteral administration may be injections, drops, lotions, ointments, gels, creams, suspensions, emulsions, suppositories, patches, or sprays, but is not limited thereto. The pharmaceutical composition may include additives such as diluents, excipients, lubricants, binders, disintegrants, buffers, dispersants, surfactants, colorants, flavors, or sweeteners, and the like, if necessary.

The pharmaceutical composition of the present invention may be administered in a therapeutically effective amount. The therapeutically effective amount refers to a drug dosage that exerts an effective medicinal effect when administered alone or in combination with other drugs. The suitable total daily dosage may be determined by the treating physician within proper medical judgment range. It is preferable to apply differently the specific therapeutically effective amount for a specific patient depending on various factors including the type and degree of the reaction to be achieved, the type and amount of anticancer drugs to be administered in combination, a specific composition used whether other agents are used in some cases, the patient's age, weight, general health status, sex and diet, time of administration, route of administration, duration of treatment, and the amount of radiation irradiated, and similar factors well known in the medical field.

In an aspect, the present invention provides a method for preventing or treating cereblon-related diseases including administering the cell-penetrating cereblon recombinant fusion protein as described above to a patient in a therapeutically effective amount.

In an aspect, the present invention provides the use of the cell-penetrating cereblon recombinant fusion protein as described above in the production of a drug for preventing or treating a cereblon-related disease.

Matters mentioned in the pharmaceutical composition, combination, treatment method and use of the present invention are applied equally as long as they are inconsistent with each other.

The novel cell-penetrating cereblon recombinant fusion protein according to the present invention may be usefully employed in the prevention or treatment of cereblon-related diseases.

Hereinafter, the present invention will be described in more detail by Examples. However, these Examples of the present invention are provided to facilitate understanding of the invention, and the scope of protection of the invention is not limited by the following Examples.

<Experimental Materials and Methods>

1. Construction of Plasmid

As a plasmid for preparation of a recombinant protein, a pET-23a vector (Novagen, Madison, Wis., USA), which is advantageous for expression in *E. coli* and purification of His tag protein, was purchased and used. The entire 30Kcα-CRBN gene was synthesized by Geneart. During the synthesis, codon optimization was performed according to the *E. coli* strain.

The 30Kcα-CRBN gene sequence (SEQ ID NO: 4) was inserted using the BamHI/XhoI restriction enzyme site in the multiple cloning site (MCS) of the pET-23a vector.

Specifically, first, each vector and insert added with EcoRI/XhoI enzyme (NEB) and a custom buffer were cultured for 18 hours in a heat block at 37° C. Next, the insert and vector were subjected to electrophoresis on an agarose gel, and then each insert and vector were extracted from the gel using AccuPrep® PCR/Gel DNA Purification Kit (Bionia). The extracted insert and vector were mixed in a ratio of 3:1, and then T4 ligase (Cat No. M0202M from NEB) was added and cultured for 18 hours. The resulting plasmid was transformed into DH5a competent cells (Cat. No. RH617-J80 from RBC), and then only ampicillin-resistant colonies were selected and cultured in 2 ml of LB broth media (0.1% ampicillin) for 12 hours. The plasmid was extracted from the cell pellets using AccuPrep® Nano-Plus Plasmid Extraction Kit, and the final nucleotide sequence was confirmed.

2. Preparation and Purification of Recombinant Protein

The plasmid extracted according to the above-described procedure was transformed into BL21 cells, put into LB broth medium, and cultured in a shaker incubator. The product was treated with IPTG 1 mM, and cultured for 4 hours. Cell lysates were obtained using a centrifuge and lysed using a sonicator. Then, the protein was purified using FPLC (GE Healthcare), followed by dialysis, and stored. As purification buffers, lysis buffer (20 mM Tris-HCl, 0.5 M NaCl, 20 mM imidazole, pH 8.0), washing buffer (20 mM Tris-HCl, 0.5 M NaCl, 50 mM imidazole, pH 8.0), elution buffer (20 mM Tris-HCl, 0.5 M NaCl, 350 mM imidazole, pH 8.0), and dialysis buffer (20 mM Tris-HCl buffer (pH 8.0)) were used.

The purified protein was loaded on an SDS-PAGE gel (Cat. No. 456-1086 from Bio-Rad) and subjected to electrophoresis. The gel was stained with a staining buffer (Cat. No. LC6060 from Invitrogen). Then, the thus-obtained protein (a fusion recombinant protein having a structure of N'-30Kcα-CRBN-C') was finally confirmed (FIG. 1).

Experimental Example

Experimental Example 1: Confirmation of Cell-Penetrating Ability of Cell-Penetrating Peptide Dimer Using Immunocytochemistry The MM1.S cell line (American Type Culture Collection, ATCC from USA) was incubated in RPMI1640 medium containing 10% FBS and 1% penicillin/streptomycin at 37° C. under 5% CO2. The Lenalidomide-resistant MM1.S cell line was established by gradually adding 10 mL of lenalidomide (Sigma-Aldrich, Cat No. D2438) from 5 μM to 200 μM to the cell line culture.

In order to evaluate cytotoxic effects of the 30Kcα-CRBN recombinant fusion protein, 1×104 MM1.S lenalidomide-resistant cells were seeded in each well of a 96 well plate. 200 μM of lenalidomide and/or 3 μM of 30Kcα-CRBN recombinant fusion protein were added to each well according to the experimental group. The total medium volume of each well was adjusted to 100 μL. Then, each medium was cultured for 42 hours, and 10 μl of EZ-Cytox (Cat. No. EZ-3000 from Dogen) was added to each well, followed by incubation for 3 hours. Thereafter, absorbance was measured at 450 nm using a microplate reader (Clarostar™ from BMGlabtech), and a cell viability (%) was calculated by using the measured absorbance and shown in FIG. 2.

It was confirmed that when the 30Kcα-CRBN recombinant fusion protein was not used but lenalidomide was used alone, the cell viability of the MM1.S cell line could not be reduced, and thus the resistance to lenalidomide was obtained in the cell line (FIG. 2A). On the other hand, it was confirmed that when the 30Kcα-CRBN recombinant fusion protein and lenalidomide were used in combination, the cell viability of the lenalidomide-resistant cell line was significantly reduced by nearly 50% compared with the control (FIG. 2B).

Therefore, the above Examples show that the 30Kcα-CRBN recombinant fusion protein according to the present invention is capable of being usefully employed in an alternative anticancer therapy that overcomes the limitations of existing anticancer treatments, such as anticancer drug-resistant cancer treatment.

What is claimed is:

1. A cell-penetrating recombinant fusion protein comprising a peptide domain consisting of the amino acid sequence of SEQ ID NO: 1 and a peptide domain consisting of the amino acid sequence of SEQ ID NO: 2.

2. A pharmaceutical composition comprising the cell-penetrating recombinant fusion protein of claim 1, and a cereblon-targeting drug,
   wherein the cereblon-targeting drug is an immunomodulatory imide drug (IMiD), a proteolysis targeting chimera (PROTAC) compound comprising a cereblon-targeting moiety having an imide group, or a combination thereof.

\* \* \* \* \*